United States Patent
Sugimoto et al.

(10) Patent No.: US 10,288,606 B2
(45) Date of Patent: May 14, 2019

(54) ANALYSIS METHOD AND ANALYSIS KIT FOR SIMULTANEOUSLY DETECTING OR QUANTITATING MULTIPLE TYPES OF TARGET SUBSTANCES

(71) Applicant: UNIVERSAL BIO RESEARCH CO., LTD., Matsudo-shi, Chiba (JP)

(72) Inventors: Takaki Sugimoto, Matsudo (JP); Tetsuya Ueda, Matsudo (JP); Shuichi Kobayashi, Matsudo (JP); Hideji Tajima, Matsudo (JP)

(73) Assignee: UNIVERSAL BIO RESEARCH CO., LTD., Matsudo-Shi, Chiba (JP)

( * ) Notice: Subject to any disclaimer, the term of this patent is extended or adjusted under 35 U.S.C. 154(b) by 699 days.

(21) Appl. No.: 14/437,450

(22) PCT Filed: Oct. 21, 2013

(86) PCT No.: PCT/JP2013/078406
§ 371 (c)(1),
(2) Date: Apr. 21, 2015

(87) PCT Pub. No.: WO2014/065221
PCT Pub. Date: May 1, 2014

(65) Prior Publication Data
US 2015/0276728 A1 Oct. 1, 2015

(30) Foreign Application Priority Data
Oct. 22, 2012 (JP) ................................ 2012-232488

(51) Int. Cl.
*G01N 33/00* (2006.01)
*G01N 33/543* (2006.01)
(Continued)

(52) U.S. Cl.
CPC ... *G01N 33/54306* (2013.01); *G01N 21/6428* (2013.01); *G01N 21/76* (2013.01);
(Continued)

(58) Field of Classification Search
CPC ................................................. G01N 33/54306
(Continued)

(56) References Cited

U.S. PATENT DOCUMENTS

| 5,861,124 A * | 1/1999 | Hosoi | C12Q 1/68 204/452 |
| 6,846,453 B1 | 1/2005 | Uesaka et al. | |

(Continued)

FOREIGN PATENT DOCUMENTS

| JP | 57-70459 A | 4/1982 |
| JP | 2000-356638 A | 12/2000 |

(Continued)

OTHER PUBLICATIONS

Kagawa et al. "Automated single nucleotide polymorphism typing using bead array in capillary tube" Journal of Bioscience and Bioengineering vol. 110 No. 4, 505-508, 2010 (Year: 2010).*

(Continued)

*Primary Examiner* — Christine T Mui
*Assistant Examiner* — Emily R. Berkeley
(74) *Attorney, Agent, or Firm* — Birch, Stewart, Kolasch & Birch, LLP

(57) ABSTRACT

The present invention provides an analysis method for simultaneously detecting or quantifying plural species of target substances by measuring the light emission from plural carriers within a single container from outside of the container, these carriers comprising a plurality of substances that are respectively immobilized thereon for capturing the plural species of target substances, wherein the light emission from a desired carrier is selectively received by mea- (Continued)

suring the emission from the carriers through an optical filter. The present invention also provides an analysis kit for simultaneously detecting or quantifying plural species of target substances by measuring the light emission from plural carriers within a single container from outside of the container, these carriers comprising a plurality of substances that are respectively immobilized thereon for capturing the plural species of target substances, which comprises the plural carriers and an optical filter for selectively receiving the emission from a desired carrier.

8 Claims, 2 Drawing Sheets

(51) Int. Cl.
  *G01N 21/64* (2006.01)
  *G01N 21/76* (2006.01)
  *G01N 21/77* (2006.01)
(52) U.S. Cl.
  CPC ............... *G01N 33/54313* (2013.01); *G01N 2021/7793* (2013.01); *G01N 2333/59* (2013.01)
(58) Field of Classification Search
  USPC ........................................................ 436/164
  See application file for complete search history.

(56) References Cited

U.S. PATENT DOCUMENTS

| 2011/0136250 | A1* | 6/2011 | Ran | G01N 21/6428 |
| | | | | 436/164 |
| 2011/0189714 | A1* | 8/2011 | Ayliffe | C12M 47/04 |
| | | | | 435/29 |
| 2012/0094307 | A1* | 4/2012 | Tajima | G01N 33/54313 |
| | | | | 435/7.4 |

FOREIGN PATENT DOCUMENTS

| JP | 2008-35778 A | 2/2008 |
| JP | 2011-75491 A | 4/2011 |
| JP | 2012-233888 A | 6/2011 |
| WO | WO 2010/122990 A1 | 10/2010 |
| WO | WO 2011/064778 A2 | 6/2011 |

OTHER PUBLICATIONS

Mitani et al. "Rapid SNP diagnostics using asymmetric isothermal amplification and a new mismatchsuppression technology" Nature Methods | vol. 4 No. 3 | Mar. 2007 | 257-262 (Year: 2007).*
International Search Report, issued in PCT/JP2013/078406, dated Nov. 12, 2013.
International Preliminary Report on Patentability and English translation of the Written Opinion of the International Searching Authority (Forms PCT/IB/338, PCT/IB/373 and PCT/ISA/237), dated May 7, 2015, for International Application No. PCT/JP2013/078406.

* cited by examiner (1)  (2)

(3)

ANALYSIS METHOD AND ANALYSIS KIT FOR SIMULTANEOUSLY DETECTING OR QUANTITATING MULTIPLE TYPES OF TARGET SUBSTANCES

TECHNICAL FIELD

The present invention relates to an analysis method and an analysis kit for simultaneously detecting or quantifying plural species of target substances.

BACKGROUND ART

BIST™ (Beads array In Single Tip) technology has been developed as a technique for simultaneously detecting a plurality of target substances for analysis (Non-Patent Document No. 1). BIST™ is a device comprising probe beads 1 mm in diameter aligned and sealed in a cylindrical tip (hereinafter, referred to as "capillary"). These beads individually carry an immobilized biological molecule (e.g., antibody, antigen or DNA fragment) that binds to a target substance for measurement such as antigen or gene. Since this BIST™ can fit to the nozzle of a Magtration™ apparatus, it is possible to carry out hybridization or antigen-antibody reaction and washing operation using the same automated apparatus that is used for nucleic acid extraction (e.g., Magtration™ System 6GC or Magtration™ System 12GC plus, both manufactured by Precision System Science). The signal generated therefrom is detected with a scanner (e.g., BIST™nner manufactured by Precision System Science).

The biggest technical feature of BIST™ is that a plurality of probe beads for capturing different target substances are aligned in a capillary, thus enabling simultaneous detection of multi-items. In the application of BIST™ to quantitative examination of thyroid stimulating hormone (TSH), as well as FT3 (Free Triiodo thyronine) and FT4 (Free Thyroxine) which are clinically highly useful when examined simultaneously with TSH, the range of detection concentrations required in practice extends broadly (TSH: 0.05-50 μIU/mL, FT3: 0.5-20 pg/mL, FT4: 0.1-10 ng/dL; approximately $10^3$ in dynamic range). For this reason, in order to perform multi-item simultaneous examination, the signal light from each probe bead (light whose intensity increases in proportion to the concentration of the target substance) should be localized to thereby suppress the interference with the signal light from other probe beads. However, no satisfactory localization of signal light has yet been achieved to date.

PRIOR ART LITERATURE

Non-Patent Documents

Non-Patent Document No. 1: Simple Determination of Genetic Polymorphism; 2008 September Issue of "Monthly Bio Industry" published by CMC Publishing Co., Ltd.

DISCLOSURE OF THE INVENTION

Problem for Solution by the Invention

It is an object of the present invention to localize the signal light from probe beads in order to simultaneously detect or quantify plural species of target substances.

Means to Solve the Problem

As a result of intensive and extensive researches, the present inventors have found that the light emitted from a desired probe bead can be selectively received by measuring the emission from the probe beads through an optical filter. Thus, the present invention has been achieved.

A summary of the present invention is as described below.

(1) An analysis method for simultaneously detecting or quantifying plural species of target substances by measuring the light emission from plural carriers within a single container from outside of the container, these carriers comprising a plurality of substances that are respectively immobilized thereon for capturing the plural species of target substances, wherein the light emission from a desired carrier is selectively received by measuring the emission from the carriers through an optical filter.

(2) The method according to (1), wherein the optical filter is located on the surface of the container or made of the container itself (3) The method according to (1) or (2), wherein the optical filter is made of the container itself (4) The method according to any one of (1) to (3), wherein the optical filter has a light transmittance of 70% or less in the wavelength band of emission from the target of measurement.

(5) The method according to any one of (1) to (4), wherein the carriers are spherical.

(6) The method according to any one of (1) to (5), wherein the carriers are arranged one-dimensionally or two-dimensionally.

(7) The method according to any one of (1) to (6), wherein the emission is chemiluminescence or fluorescence and has a wavelength band within the range of 340-900 nm.

(8) An analysis kit for simultaneously detecting or quantifying plural species of target substances by measuring the light emission from plural carriers within a single container from outside of the container, these carriers comprising a plurality of substances that are respectively immobilized thereon for capturing the plural species of target substances, which comprises the plural carriers and an optical filter for selectively receiving the emission from a desired carrier.

(9) The analysis kit according to (8), wherein the optical filter is made of the container itself.

(10) The analysis kit according to (8) or (9), wherein the emission is chemiluminescence or fluorescence and has a wavelength band within the range of 340-900 nm.

Effect of the Invention

According to the present invention, it has become possible to design a system for simultaneously detecting or quantifying plural species of target substances, in which the signal light from a desired probe bead carrying an immobilized substance for capturing a target substance is localized to inhibit interferences with the signal light from other probe beads.

The present specification encompasses the contents of the specification and/or the drawings disclosed in Japanese Patent Application No. 2012-232488 based on which the present patent application claims priority.

BRIEF DESCRIPTION OF THE DRAWINGS

FIG. 2-1 (upper left panel) shows emission peaks derived from the probe bead positioned at the central part of a capillary in the measurement of TSH (0.5 μIU/mL) with BIST™.

FIG. 2-2 (upper right panel) shows emission peaks derived from the probe bead positioned at the central part of a capillary in the measurement of TSH (25 μIU/nip with BIST™.

FIG. 2-3. (lower panel) shows the relation between the absorbance of the capillary material and the value of signal light peak.

FIG. 3

FIG. 3.1 (upper left panel) is a graph obtained by normalizing the data from FIG. 2-2 with the peak value and representing the vertical axis on a log scale.

FIG. 3.2 (upper right panel) shows the relation between the absorbance of capillary material and the peak width (width which makes the vertical axis 1/3000 ).

FIG. 3.3 (lower panel) shows the relation between the absorbance of capillary material and the ratio of peak value to peak width (P/W ratio). (Relative P/W ratios are plotted, with the P/W ratio at Abs=0.0 taken as unity.)

BEST MODES FOR CARRYING OUT THE INVENTION

Figure 1:
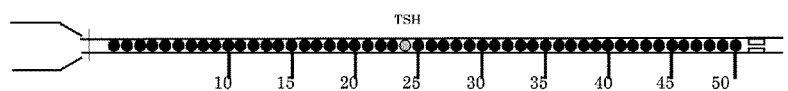
FIG. 1 This figure shows the inner structure of BIST™ capillary.

Hereinbelow, the embodiment of the present invention will be described in detail.

The present invention provides an analysis method for simultaneously detecting or quantifying plural species of target substances by measuring the light emission from plural carriers within a single container from outside of the container, these carriers comprising a plurality of substances that are respectively immobilized thereon for capturing the plural species of target substances, wherein the light emission from a desired carrier is selectively received by measuring the emission from the carriers through an optical filter.

The container may be of any type as long as light emission can be measured from the outside thereof. The container may be light-transmissive and it is preferably made of a light-transmitting material such as resin or glass. The shape of the container is not particularly limited, but it may be a thin tube or a pipette-like shape. For example, the container to be used in BIST™ is a cylindrical tip from which a liquid contained therein can be discharged by suction.

In the method of the present invention, it is possible to reduce the diffusion of the signal light by increasing the transparency of the container. Haze value for 1 mm thickness of the container may be 20% or less, preferably 10% or less, and more preferably 1% or less. Specific examples of materials for the container which give a haze value of 20% or less for 1 mm thickness include, but are not limited to, polypropylene, polycarbonate, polystyrene, polymethyl methacrylate, cyclic polyolefin and polymethylpentene.

Haze value is a value representing the degree of transparency. In JIS K7136, haze value is defined as a ratio of diffusion transmittance to total light transmittance.

Further, the refractive index of the container in the wavelength band of light emission or radiation may be 1.6 or less, preferably 1.55 or less, and more preferably 1.50 or less. Specific examples of materials for the container which give a refractive index of 1.6 or less include, but are not limited to, polypropylene, polycarbonate, polystyrene, polymethyl methacrylate, cyclic polyolefin and polymethylpentene.

Target substances may be substances to be analyzed which are contained in biological samples such as blood, serum, urine, lymph, oral mucosa, nail or sputum, or samples as from river water, lake water, sea water or soil. Specific examples of target substances include, but are not limited to, biological substances such as nucleic acids, proteins, antigens, antibodies, enzymes or saccharides; bacteria such as *Salmonella enterica* or *Escherichia coli*; and metals such as cobalt, iron, molybdenum, copper, zinc, arsenic, cadmium or vanadium.

Target substances may be labeled in a measurable manner. Specific examples of measurable labeling include, but are not limited to, fluorescence labeling, chemiluminescence labeling, electrochemiluminescence labeling, enzyme labeling, radiolabeling and magnetic labeling. Specific examples of labeling substances include, but are not limited to, fluorescent substances such as Marine Blue, Cascade Blue, Cascade Yellow, Fluorescein, Rhodamine, Phycoerythrin, CyChrome, PerCP, Texas Red, Allophycocyanin, PharaRed, Oregon Green-488, Cy dyes (e.g., Cy2, Cy3, Cy3.5, Cy5, Cy7, etc.), Alexa dyes (e.g., Alexa-488, Alexa-532, Alexa-546, Alexa-633, Alexa-680, Alexa-700, Alexa-750, etc.) and BODIPY dyes (e.g., BODIPY FL, BODIPY TR-, etc.); chemiluminescent substances such as luminol, acridine, adamantyl dioxetane, oxalic acid ester, lophine, lucigenin, and isoluminol derivatives; electrochemiluminescent substances such as tris-bipyridine-(4-methyl sulfone) NHS ester ruthenium(II) complex, diphenylanthracene and tetraphenylanthracene; and enzymes such as POD (hydrogen peroxidase), AP (alkaline phosphatase), β-galactosidase, glucose oxidase, glucose oxidase and glucose-6-phosphate dehydrogenase. In addition to the above-mentioned substances, radioactive substances such as radioisotopes (e.g., $^3H$, $^{14}C$, $^{32}P$, $^{33}P$, $^{35}S$, $^{125}I$, etc.) may also be used for labeling.

Target substances may be labeled either directly or indirectly. For example, sandwich ELISA is used in the Example described later. Specifically, a target substance (which is an antigen) binds to a primary antibody immobilized on a carrier; then, a biotin-labeled antibody (secondary antibody) binds to the target substance. Subsequently, HRP conjugated with streptavidin which catalyzes chemiluminescence binds to the secondary antibody to thereby label the target substance.

Substances for capturing target substances may be any substances which bind to the target substance. Specific examples of such substances include, but are not limited to, antibodies, antigens, DNA fragments, metal complexes, and other low molecular weight compounds.

Carriers may take any shape such as amorphous particles, spheres (beads), yarn (strand), magnetic beads, etc. Preferably, the shape is spherical. When carriers take the shape of beads or magnetic beads, it is preferred that substances for capturing different target substances are respectively immobilized on different beads or magnetic beads. When carriers take the shape of yarn, it is preferred that substances for capturing different target substances are respectively immobilized at different positions of the yarn. In BIST™, carriers take the shape of spheres (beads).

Spheres (beads) may be about 1 mm in size and made of such materials as plastic or ceramic. Such beads are disclosed in, for example, Japanese Unexamined Patent Publication No. 2000-346842 and Japanese Unexamined Patent Publication (Translation of PCT Application) No. Hei14-534657.

Magnetic beads may be several ten micrometers in size and may be prepared by mixing iron powder or the like with plastic or ceramic or the like and magnetizing the resultant mixture. Such magnetic beads are disclosed in, for example, Japanese Unexamined Patent Publication No. Hei8-62224 (Japanese Patent No. 3115501), WO96/29602 and WO97/44671.

Yarn (strand) may be about 0.1 mm in diameter and made of a resin material. Such yarn is disclosed in, for example, Japanese Unexamined Patent Publication No. 2006-214759, WO01/53831 and WO2003/7901.

Carriers may be arranged one-dimensionally or two-dimensionally. The expression "carriers are arranged one-dimensionally" means such a state that the positional information necessary for specifying the carrier from which the observed light signal is derived is one-dimensional. For example, in BIST™, it can be said that carriers (beads) are arranged in one-dimensionally. The expression "carriers are arranged two-dimensionally" means such a state that the positional information necessary for specifying the carrier from which the observed light signal is derived is two-dimensional. For example, in a measuring kit wherein a single layer of carriers is spread all over a plate, it can be said that carriers are arranged two-dimensionally.

Substances for capturing target substances are immobilized on carriers by means of covalent bonding, chemical adsorption, physical adsorption, electrical interaction, hydrophobic interaction, van der Waals force, hydrogen bond, and so forth.

Analysis of target substances may be performed by contacting substances for capturing the target substances with the target substances, both being immersed in a liquid, and measuring the light emission generated thereafter.

In the method of the present invention, it is possible to selectively receive the light emission from a desired carrier by measuring the emission from the carriers through an optical filter.

In the present specification, the expression "selectively receive the light emission from a desired carrier" means suppressing optical intersections among plural carriers, as exemplified by a method in which light that propagates through the capillary wall in BIST™ or light that is incident oblique to the line normal to the light receiving surface is selectively shielded with respect to the normal incident light. Besides, the above expression also encompasses reduction of the effect of background light.

In the present specification, the expression "optical intersections of emission signals from plural carriers" refers to a state wherein emission signals from plural carriers are received by a detector simultaneously so that those emission signals cannot be isolated from each other.

The diffusion of signal light can be reduced by measuring the light emission through an optical filter. An optical filter whose light transmittance in the wavelength band of emission from the target of measurement is 70% or less may be used. The light transmittance in the wavelength band of emission from the target of measurement is preferably 8-70%, and more preferably 20-60%.

The optical filter may be prepared by coloring a suitable material (e.g., polypropylene, polycarbonate, polystyrene, polymethyl methacrylate, cyclic polyolefin, polymethylpentene, polyethylene terephthalate and the like) with a colorant (e.g., anthraquinone colorants, perinone colorants, heterocyclic colorants, carbon black, titanium oxide and the like).

The optical filter may be provided separately from a container. Alternatively, a container itself may be used as an optical filter. When an optical filter is provided separately from a container, the filter may be located on the surface of the container. For example, the optical filter may be tightly adhered to the container wall in conformity with its shape.

Light emission may be chemiluminescence, fluorescence, electrochemiluminescence or the like. Preferably, light emission is chemiluminescence or fluorescence, with its wavelength band being 340-900 nm. Light emission may be measured from outside of the container using known techniques such as fluorometer, spectrophotometer, scintillation counter, photodiode, CCD, CMOS, photomultiplier, and the like.

In the method of the present invention, plural species of target substances are detected or quantified simultaneously. The term "plural species" means at least two species, for example, two, three, four, five or more species. Substances for capturing the plural species of target substances are respectively immobilized on plural carriers. In the case of BIST™, for example, probe beads (on which substances for capturing target substances are immobilized) and light-shielding beads, totaling about 50 in number, may be aligned in a capillary with a total length of 50 mm. The probe beads may comprise a blank and an internal standard. "Blank" means a carrier on which no capturing substance is immobilized. "Internal standard" means a carrier on which a substance is immobilized for capturing a standard substance of a known concentration that cannot be contained in the sample for analysis but which is added just before analysis.

For simultaneous detection or quantification of plural species of target substances, since a capturing substance specifically captures the target substance regardless of whether other capturing substances are present, plural carriers on which different types of capturing substances have been immobilized are arranged in the same container and then a liquid sample is brought into contact with these carriers. As a result, plural species of target substances can be detected simultaneously.

The present invention also provides an analysis kit for simultaneously detecting or quantifying plural species of target substances by measuring the light emission from plural carriers within a single container from outside of the container, these carriers comprising a plurality of substances that are respectively immobilized thereon for capturing the plural species of target substances, which comprises the plural carriers and an optical filter for selectively receiving the emission from a desired carrier.

The carrier, optical filter, container and light emission are as defined above.

Hereinbelow, the present invention will be described in more detail with reference to the following Example. However, the scope of the present invention is not affected by such description or the Example.

EXAMPLE

BIST™ (Bead array In Single Tip) has been developed as a technology for capturing/detecting target substances such as antigens, genes, etc. using probe beads 1 mm in diameter on which biological molecules such as antibodies, nucleic acids, etc. are immobilized. The biggest technical feature of BIST™ is that a plurality of probe beads for capturing different target substances are aligned in a cylindrical tip (hereinafter, referred to as "capillary") to enable simultaneous detection of multi-items. In the application of BIST™ to quantitative examination of thyroid stimulating hormone (TSH), as well as FT3 and FT4 which are clinically highly useful when examined simultaneously with TSH, the range of detection concentrations required in practice extends broadly (TSH: 0.05-50 µIU/mL, FT3: 0.5-20 pg/mL, FT4: 0.1-10 ng/dL; approximately $10^3$ in dynamic range). For this reason, in order to perform multi-item simultaneous examination, the signal light from each probe bead (light whose intensity increases in proportion to the concentration of the target substance) should be localized to thereby suppress the interference with the signal light from other probe beads. In the following Example, the effect of capillary coloring was examined for the purpose of localization of signal light.

1. Summary

In the detection of TSH with a capillary about 50 mm in total length, capillaries colored with black pigments of six density levels were used to detect TSH (antigen concentrations: 0.5 and 25 µIU/mL). As a result, the effect of capillary coloring was markedly observed at the TSH antigen concentration of 25 µIU/mL providing the higher intensity of signal light. The aspect ratio of peak [(peak height)/(⅓₀₀₀ width)] increased by approximately 1.8-fold at maximum, compared to the ratio when capillary coloring was not performed. It was thus confirmed that capillary coloring is effective for localizing signal light and is a useful technique for achieving multi-item detection in BIST™.

2. Experimental Methods 2-1 Capillary Coloring and Measurement of Transmittance

Polycarbonate pellets (CALIBRE™) manufactured by Sumitomo Dow Limited were colored with a colorant of Sunny Color Co., Ltd. (Dry color Y-4-6033 smoke) at five density levels to prepare colored pellets (having transmittancees of approximately 7.7%, 19%, 28%, 62% and 70% at 426 nm through a thickness of 1 mm).

Subsequently, the resultant colored pellets were processed into sheets (1 mm thick x 3 mm square) to thereby prepare test pieces for measuring transmittance.

The transmittances of these test pieces were measured with a Hitachi High Technologies spectrophotometer (U-3000) over the wavelength range of 340-1000 nm.

2-2 Preparation of BIST™ for TSH Measurement 2-2-1 Preparation of Antibody-Immobilized Beads 2-2-1-1 Probe beads (n=30) were mixed and washed with 1×PBS (1 mL) in a sample tube by inverting the tube several times. This operation was repeated twice. Subsequently, the liquid was thoroughly removed from the tube, and 300 µL (10 µL/bead) of 1×PBS, 20 µg/mL TSH; TSH183 were added thereto. The tube was left standing overnight (19 hr) at 4° C. for immobilizing the antibody on the beads as a solid layer.

2-2-1-2 After antibody immobilization, the beads were mixed and washed with 1 mL of 1×PBS, 0.05% Tween 20 in a sample tube by inverting the tube several times. This operation was repeated twice. Subsequently, the liquid was thoroughly removed from the tube, and 300 µL, (10 µL/bead) of 1×PBS, 0.1% Tween 20, 1% (w/w) Block Ace were added thereto. The tube was left standing at room temperature for 3 hours for blocking.

2-2-1-3 After blocking, the beads were mixed and washed with 1 mL of 1×PBS, 0.05% Tween 20 in a sample tube by inverting the tube several times. This operation was repeated twice. Subsequently, the liquid was thoroughly removed from the tube, which was then filled with 1×PBS.

2-2-2 Preparation of Light-Shielding Beads 2-2-2-1 SiC beads (6.88 g) were weighed out (approximately 4000 beads), and then mixed and washed with 15 mL of 1×PBS in a tube by inverting the tube several times. This operation was repeated twice. Subsequently, the liquid was thoroughly removed from the tube, and 15 mL of 1×PBS, 0.1% Tween 20, 1% (w/w) Block Ace were added thereto. The tube was gently stirred with a rotator at room temperature for 1 hour for blocking.

2-2-2-2 After blocking, the beads were mixed and washed with 15 mL of 1×PBS, 0.05% Tween 20 in a tube by inverting the tube several times. This operation was repeated twice. Subsequently, the liquid was thoroughly removed from the tube, which was then filled with 1×PBS. Those beads which were not for immediate use were stored at 4° C.

2-2-3 Preparation of BIST™

One TSH probe bead and 49 light-shielding beads were filled in a capillary as shown in FIG. 1.

2-2-4 Detection of TSH 2-2-4-1 As shown in the Table below, reagents were added to GC series cartridges (Precision System Science Co., Ltd.), which were then mounted on SX-12GC (Precision System Science Co., Ltd.). BIST™ together with Sheath DN-100 (Precision System Science Co., Ltd.) were set at Hole-2 of SX12GC combo rack (Precision System Science Co., Ltd.). The reaction was completed in about 110 minutes.

2-2-4-2 After completion of the reaction, the solution contained in well 1 was transferred into a capillary and stored until use for measurement. Immediately before measurement, the solution was removed from within the capillary, which was then charged with 80 µL of detection reagents (ECL Western Detection Reagents; GE Health Care Japan) by suction. Subsequently, TSH was measured with LuBEA™ (Precision System Science Co., Ltd.) equipped with a PMT (photomultipulator) and a scanning-type optical fiber detection probe.

TABLE 1

| | Contents of Cartridge | Buffer | Amount of Addition | No. of Times of Stirring |
|---|---|---|---|---|
| well 1 | Wash 3-3 | Wash Buffer | 100 ul | 10 times |
| well 2 | TSH 0~100 uIU/ml | Binding Buffer | 100 ul | 300 times (30 min) |
| well 3 | Wash 1-1 | Wash Buffer | 100 ul | 10 times |
| well 4 | Wash 1-2 | | 100 ul | 10 times |
| well 5 | Wash 1-3 | | 100 ul | 10 times |
| well 6 | Biotin-Labeled Antibody 1/500 | Binding Buffer | 100 ul | 300 times (30 min) |
| well 7 | Wash 2-1 | Wash Buffer | 100 ul | 10 times |
| well 8 | Wash 2-2 | | 100 ul | 10 times |
| well 9 | Wash 2-3 | | 100 ul | 10 times |
| well 10 | Streptavidin-HRP 1/5000 | Binding Buffer | 100 ul | 300 times (30 min) |
| well 11 | Wash 3-1 | Wash Buffer | 200 ul | 10 times |
| well 12 | Wash 3-2 | | 100 ul | 10 times |
| | | | | Total 110 min |

Figure 2:
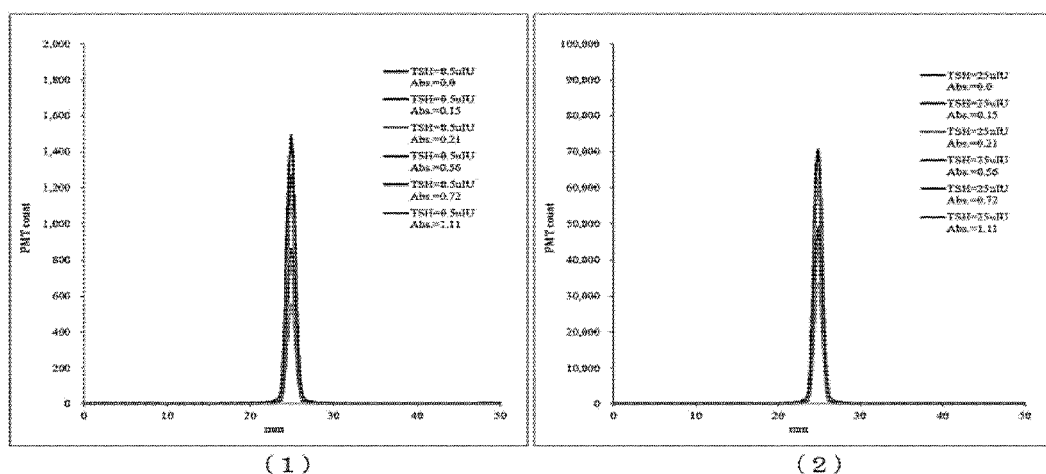
FIG. 2
Figure 2:
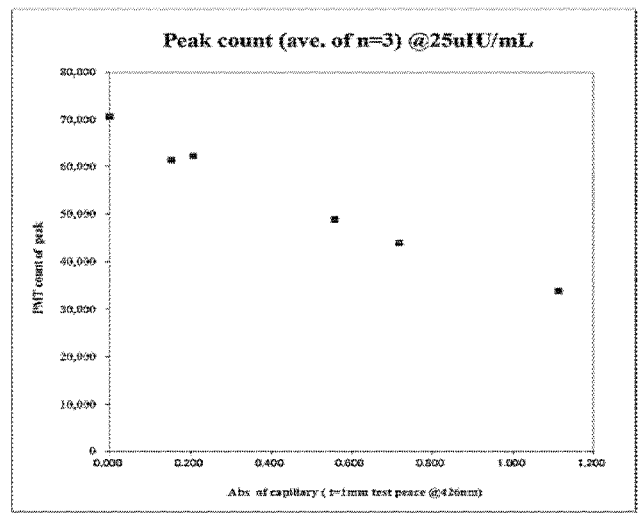
Figure 3:
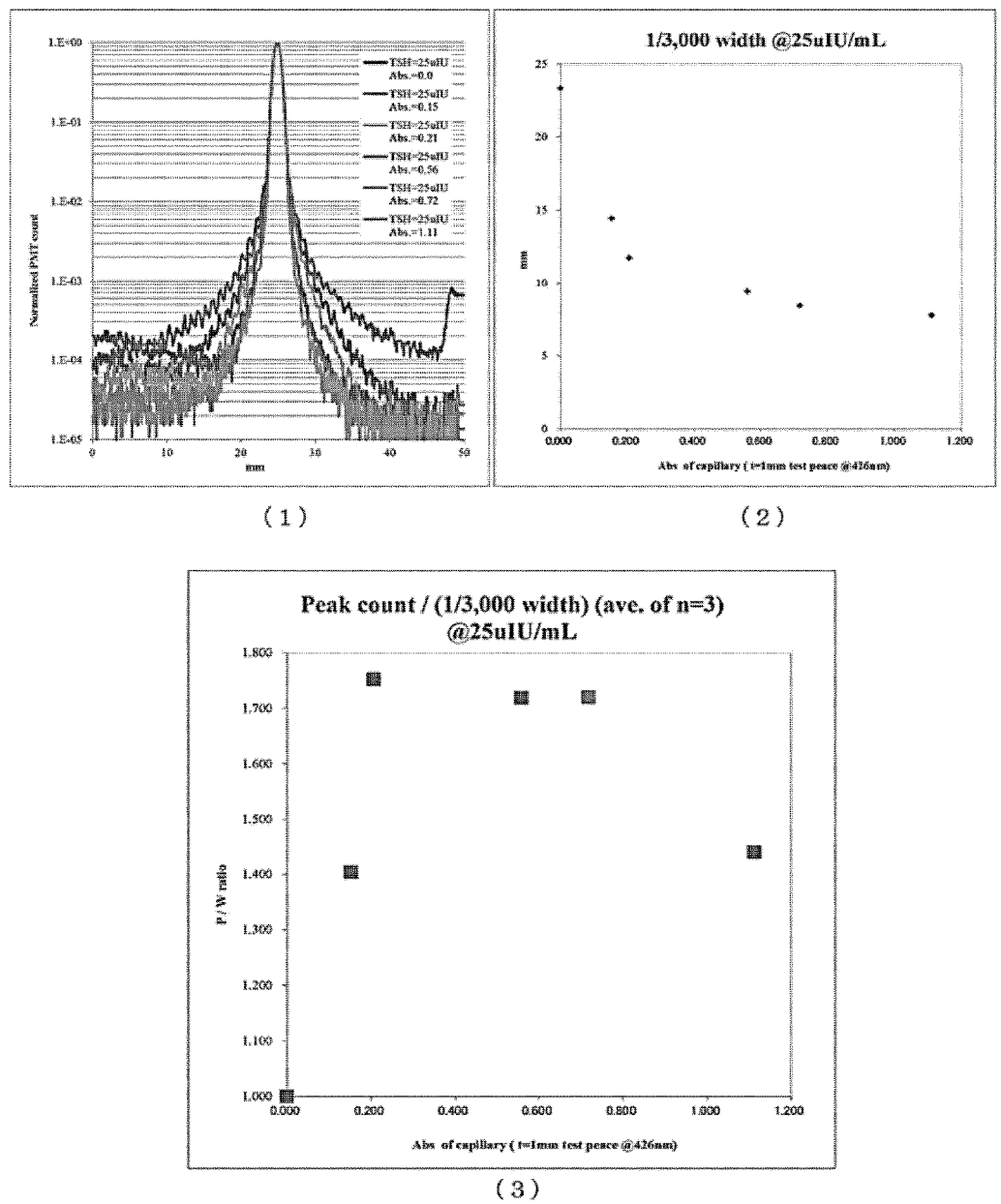

Wash Buffer: PBS
Binding Buffer: PBS
TSH: Human TSH (human thyroid stimulating hormone (derived from human serum))
Biotin-Labeled Antibody: Anti-human TSH antibody labeled with biotin
Streptavidin-HRP: manufactured by Thermo Scientific 3. Results Scanning profiles (raw data) obtained by measuring TSH at antigen concentrations of 0.5 and 25 µIU/mL with BIST™ are shown in FIG. 2-1 and FIG. 2-2. The relation between the absorbance of the capillary material and the peak value is shown in FIG. 2-3. The peak value of emission decreased in a substantially linear manner with the increasing absorbance of the capillary material (decreasing transmittance).

The data for the antigen concentration of 25 µIU/mL were normalized with peak value to give the data shown in FIG. 3-1; and the relation between the absorbance of the capillary material and the peak width is shown in FIG. 3-2. Peak width sharply decreased in the range from Abs=0 to 0.5. No marked change was observed in the higher absorbance range.

FIG. 3-3 shows a graph plotting the relation between the absorbance of the capillary material and the ratio of peak value to peak width (P/W ratio). P/W ratio sharply increased in the range between Abs=0 to 0.2, and reached maximum values in the range between Abs=0.2 to 0.8, whereupon the P/W ratio was about 1.7-1.8. In an even higher absorbance range, the P/W ratio decreased.

4. Discussion

The results shown in FIG. 3-3 revealed that coloring of the capillary material (shielding of signal light) is an effective means to attain the goal of localization of signal light (maximization of P/W ratio) in BIST™ and indicated the possibility of increasing the P/W ratio almost twice as much by appropriate coloring of the capillary material. These results show that one of the causes of signal light diffusion is light that propagates through the capillary wall. It is believed that coloring of the capillary material selectively reduces this component of signal light which propagates through the capillary wall.

All publications, patents and patent applications cited herein are incorporated herein by reference in their entirety.

INDUSTRIAL APPLICABILITY

The method of the present invention is applicable to detection and quantitative analysis of a plurality of biological molecules and low molecular weight molecules that bind thereto.

The invention claimed is:

1. An analysis method for simultaneously detecting or quantifying plural species of target substances comprising:
   measuring a light emission from a plurality of carriers each with a respective target substance immobilized thereon within a single tube or pipette shaped container from outside of the container to detect or quantify the plural species of target substances immobilized on the carriers,
   wherein the light emission from a desired carrier is selectively received by measuring the emission from the carrier through an optical filter made of the container itself, and
   wherein the optical filter is configured to suppress interference with the light emission from non-desired carriers.

2. The method according to claim 1, wherein the optical filter has a light transmittance of 70% or less in the wavelength band of emission from the carrier.

3. The method according to claim 1, wherein the carriers are spherical.

4. The method according to claim 1, wherein the carriers are arranged one-dimensionally or two-dimensionally.

5. The method according to claim 1, wherein the emission is chemiluminescence or fluorescence and has a wavelength band within the range of 340-900 nm.

6. The method according to claim 2, wherein the carriers are spherical.

7. The method according to claim 2, wherein the carriers are arranged one-dimensionally or two-dimensionally.

8. The method according to claim 3, wherein the carriers are arranged one-dimensionally or two-dimensionally.

* * * * *